United States Patent
Orelli et al.

(10) Patent No.: US 6,765,674 B2
(45) Date of Patent: Jul. 20, 2004

(54) PROCESS AND APPARATUS FOR THE COLORIMETRIC MEASUREMENT OF A TWO-DIMENSIONAL ORIGINAL

(75) Inventors: Adrian Von Orelli, Zürich (CH); Bruno Pfister, Niederglatt (CH)

(73) Assignee: Gretag-Macbeth AG, Regensdorf (CH)

( * ) Notice: Subject to any disclaimer, the term of this patent is extended or adjusted under 35 U.S.C. 154(b) by 0 days.

(21) Appl. No.: 09/925,748

(22) Filed: Aug. 10, 2001

(65) Prior Publication Data

US 2002/0054292 A1 May 9, 2002

(30) Foreign Application Priority Data

Nov. 8, 2000 (EP) ............................................. 00117208

(51) Int. Cl.[7] .............................. G01J 3/46; H04N 1/46
(52) U.S. Cl. ...................................... 356/402; 358/504
(58) Field of Search ................................ 382/162, 167; 358/500, 504, 505, 518, 530, 406, 487, 488, 506; 356/402; 359/197, 202; 399/17; 250/359.04, 559.05, 559.06; 348/195

(56) References Cited

U.S. PATENT DOCUMENTS

| | | | | |
|---|---|---|---|---|
| 4,505,589 A | * | 3/1985 | Ott et al. ..................... 356/402 |
| 4,907,077 A | * | 3/1990 | Schulz-Hennig et al. ... 358/516 |
| 4,933,778 A | * | 6/1990 | Tufano et al. ............... 358/488 |
| 5,047,861 A | * | 9/1991 | Houchin et al. ............. 358/247 |
| 5,149,960 A | * | 9/1992 | Dunne et al. ................ 250/226 |
| 5,200,817 A | * | 4/1993 | Birnbaum .................... 358/518 |
| 5,285,297 A | * | 2/1994 | Rose et al. .................. 358/518 |
| 5,339,176 A | * | 8/1994 | Smilansky et al. ......... 358/504 |
| 5,481,380 A | | 1/1996 | Bestmann |
| 5,537,516 A | * | 7/1996 | Sherman et al. ............. 358/1.9 |
| 5,642,202 A | * | 6/1997 | Williams et al. ............ 358/406 |
| 5,754,448 A | * | 5/1998 | Edge et al. .................. 358/516 |
| 6,005,968 A | | 12/1999 | Granger |
| 6,028,682 A | | 2/2000 | Ott et al. |
| 6,044,180 A | * | 3/2000 | Brandestini et al. ........ 382/274 |
| 6,075,888 A | * | 6/2000 | Schwartz .................... 382/167 |
| 6,459,825 B1 | * | 10/2002 | Lippincott .................. 382/312 |
| 6,466,337 B1 | * | 10/2002 | Suhr et al. .................. 358/446 |
| 2002/0122589 A1 | * | 9/2002 | Reiman et al. ............. 382/167 |

FOREIGN PATENT DOCUMENTS

| | | |
|---|---|---|
| EP | 0573069 | 12/1993 |
| EP | 0624028 | 11/1994 |
| EP | 0785672 | 7/1997 |
| EP | 1001610 | 5/2000 |

* cited by examiner

Primary Examiner—Zandra V. Smith
Assistant Examiner—Gordon J Stock
(74) Attorney, Agent, or Firm—McCarter & English LLP

(57) ABSTRACT

For the colorimetric measurement of a two-dimensional original, the original is photoelectrically scanned pixel by pixel in a first step by way of a color-enabled photoelectric scanning device. A digital color representation of the original is produced from the thereby obtained scanning data. In a second step, suitable measuring positions are determined from the digital color representation of the original by way of a computer using image processing methods. In a third step, the color measuring head is automatically moved under the control of the computer to the so determined measuring positions and the original is colorimetrically measured at those measuring positions. The color data obtained thereby can be further processed, for example for the generation of apparatus profiles for the colorimetric control of output apparatus. The scanning device is preferably a high resolution flatbed or autofeed scanner or a digital camera. The color measuring head is preferably a spectral measuring head. By the comparatively high resolution pixel by pixel scanning of the original, the measuring positions can be very exactly determined without manual input and without time consuming multiple measurements. Furthermore, artifacts caused by dirt can be recognized and corrected.

15 Claims, 5 Drawing Sheets

PROCESS AND APPARATUS FOR THE COLORIMETRIC MEASUREMENT OF A TWO-DIMENSIONAL ORIGINAL

This application claims priority under 35 U.S.C. §§119 and/or 365 to 00117208.9 filed in Europe on Aug. 11, 2000; the entire content of which is hereby incorporated by reference.

FIELD OF THE INVENTION

The invention relates to a process and apparatus for the colorimetric measurement of a two-dimensional original. More particularly, the invention relates to a process wherein a color measuring head is moved two-dimensionally relative to the original for the measurement of the original at preselected measuring positions.

BACKGROUND OF THE INVENTION

The wide-spread distribution of color-enabled computer peripherals and the generally higher quality requirements regarding the orthochromaticity of printed products, the so-called color management, which means the mutual co-ordination of all color-enabled computer peripheral apparatus (monitor, scanner, printer, etc.) as well as the colorimetric control of output apparatus, are of ever increasing importance.

The generation of manufacturer-specific or norm-specific (for example ITC) apparatus profiles is a central point of the color management. These apparatus profiles enable the conversion of apparatus specific color values into apparatus independent, and therefore commonly valid and transmittable color values. The generation of apparatus profiles is based on the characterization of the colorimetric properties of the input and output apparatus such as color printers and scanners. This requires the colorimetric evaluation of color test cards (so called test charts) as described, for example, in the ISO norm IT8. Such a test chart is commonly composed of several hundred test fields.

A number of methods exist today for the measurement of the color fields of a test chart.

For example, the color fields are individually measured by way of a handheld color measuring apparatus, which means a colorimeter or spectrometer as described, for example, in U.S. Pat. No. 5,684,582, the disclosure of which is hereby incorporated by reference in its entirety, which represents a significant amount of work for several hundred measurement fields.

Or the color fields are scanned in with a scanning handheld measuring apparatus, as described, for example, in DE-A 197 16 066, by manually moving the apparatus over the lines of the test chart. Compared to the method with individual manual measurements, the cost is massively reduced. However, the quality of the measuring results depends on the skills of the user because of the manual operation.

An apparatus is known from DE 197 22 073, the disclosure of which is hereby incorporated by reference in its entirety, wherein a line printer is reconfigured in such a way that it can capture color measurement data from fields found on the printout either simultaneously with the printing process or thereafter with an integrated color measuring head. This process has several disadvantages. If one measures after the printing, the original is not dry and the color measurement data can still change after the measurement. If one measures after the printing, the paper must be newly fed in, which can create problems during the positioning of the color measuring head on the original. Furthermore, a line printer can normally not be equipped with an illumination for transmission measurements because of space constraints. In addition, because of the non-linear path of the original through the printer, only flexible originals can be measured. The evaluation of, for example, a relatively stiff printed cardboard of a packaging is not possible. Scanning measuring apparatus determines the position of the color fields from the analysis of the measured values and therefore pose special requirements on the positioning of the color fields. The color fields must be so large or the apparatus must be moved so slowly that at least two complete measurements per field can be achieved.

U.S. Pat. No. 5,369,494, the disclosure of which is hereby incorporated by reference in its entirety, describes a measuring apparatus which can pull in an original inserted by the user and measure it strip by strip. The user must feed in the original once for each color field row of the test chart. This manual feeding creates work for the user and leaves room for manipulation errors. Strip by strip measuring apparatus work by scanning and therefore pose the above described requirements for the positioning and dimensioning of the color fields.

A further known process includes the use of a measuring apparatus mounted on an X Y displacement table which measures the test chart under the control of a computer. A typical representative of such an arrangement is the combination of applicant's apparatus sold under the names Spectralino and SpectroScan. At the beginning of the measurement process, the user must supply to the apparatus the position of the corner points of the measurement field arrangements, which represents a potential source for errors.

An apparatus is know from EP 0 847 187, the disclosure of which is incorporated by reference in its entirety, which can spectrally capture the image information of a complete printed sheet, in that a measuring bar with many measuring heads arranged in a row is moved over the original. Such an apparatus can be described as spectral scanner. With such a special scanner, a maximum of information can be quickly obtained from an original. However, such an apparatus can only be realized with high technical and financial cost, has a large space requirement, and has a low local resolution.

SUMMARY OF THE INVENTION

It is now an object of the invention to improve a process and apparatus of the generic type in such a way that the constructive and conceptional pre-requisites are created to carry out, within a short time and at an acceptable constructive cost, the complete procedure of the measuring in of a remitting or transmitting original without interaction of the user, whereby the amount of work of the user is reduced to a minimum and manipulation errors are at the same time precluded.

The solution of this object which forms the basis of this invention is achieved in the preferred embodiment in that the original is photoelectrically scanned, the measuring positions are determined from a color representation of the original, and the original is then colorimetrically measured at the measuring positions.

According to the basic aspect of the invention, the image information of the original is on the one hand electronically captured at high resolution and analyzed with image processing methods and the information about the original which is obtained from the analysis is then used on the other hand to control the positioning of the color measuring head.

The color measuring head thereby provides for the capturing of colorimetric values at the measuring positions of the original for the respective application.

The range of applications of the invention includes, for example, the capturing of the colorimetric values of the numerous color fields of a test chart, which can be used for the generation of ICC profiles, for the control of color-enabled output devices directly from the measured colorimetric values of the original, which are typically an image. The complete process of measuring in of a remitting or transmitting test chart can be carried out without the interaction of the user and within a short time. The amount of work for the user is thereby reduced to a minimum and manipulation errors can be precluded.

Depending on the respective type of the apparatus of the invention, it can also be used as a self calibrating and self profiling and thereby color binding digital camera or scanner.

BRIEF DESCRIPTION OF THE DRAWINGS

The invention will be described in more detail in the following by way of example only and by reference to the drawing, wherein.

DETAILED DESCRIPTION OF THE PREFERRED EMBODIMENTS

Figure 1:
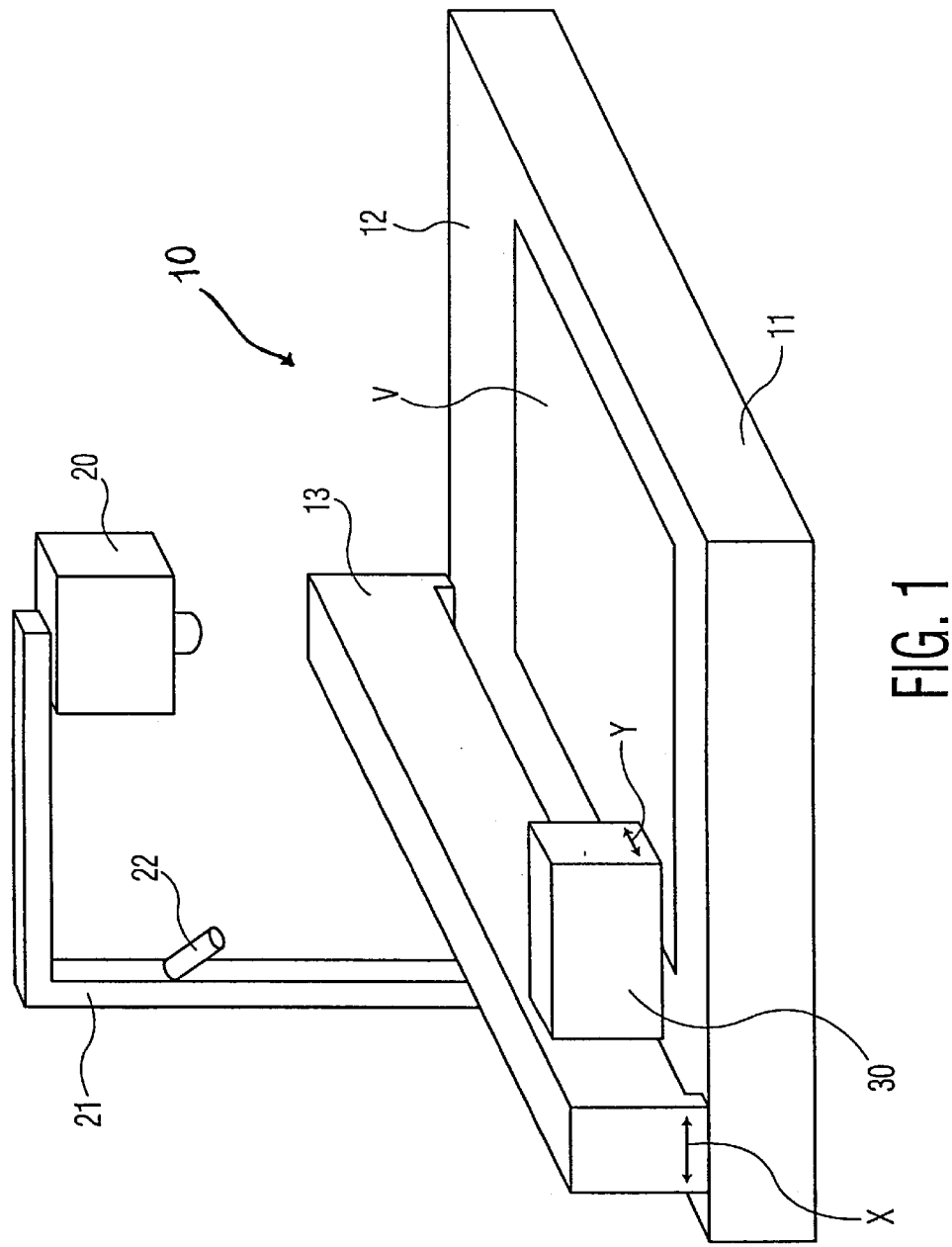
FIG. 1 shows an overall isometric view of a first embodiment of a measuring apparatus in accordance with the invention.

The first embodiment of the measuring apparatus in accordance with the invention illustrated in FIG. 1 generally includes an XY displacement table referred to by reference numeral 10 and a high resolution color-enabled image generating unit or photoelectric scanning device in the form of a digital camera 20, which is mounted above the displacement table 10 by way of a stand 21. Furthermore, an illumination device 22 is mounted on the stand 21.

The displacement table 10 includes an essentially rectangular base 11 with a supporting plate 12 for an original V to be measured (for example a color test card) as well as a bridge 13 to which a spectral measuring head 30 is mounted. The bridge 13 is moveable by way of a not-illustrated motor drive in direction of the double arrow X parallel to a longitudinal side of the base. The spectral measuring head 30 is moveably supported on the bridge 13 for displacement by way of a not-illustrated motor drive in direction of the double arrow Y parallel to the transverse side of the base. By displacement of the bridge in direction X and displacement of the spectral measuring head on the bridge in direction Y, the spectral measuring head 30 can be moved to any desired measuring position on the original V placed on the supporting plate 12 whereby the control of the movement of the spectral measuring head is carried out by a computer R (FIG. 2) which includes the details of the measuring positions to be reached. The computer R also controls the initiation of the measurement procedures of the spectral measuring head 30 and the transfer of the measured data obtained thereby (here spectral measurement data) into a memory of the computer.

The spectral measuring head 30 is constructed as a combined remission/transmission measuring head in a known manner. The supporting plate 12 is transparent for transmission measurements and an illumination arrangement is provided in the base which is here not illustrated and which homogeneously as possible illuminates the useable surface of the supporting plate 12 which can be covered by the spectral measuring head 30. The computer controlled displacement table 10 and the spectral measuring head 30 therefore correspond wholly and totally to the prior art so that the person skilled in the art does not require any further explanation in relation thereto. An example for a known spectral measuring head and a known displacement table are the apparatus sold by the applicant under the type "Spectrlino" or "SpectroScan". A spectral measuring head suited for the present invention is also described, for example, in U.S. Pat. No. 6,043,983, the disclosure of which is hereby incorporated by reference in its entirety. In place of the spectral measuring head, an also conventional three range or similar color measuring head can be provided.

The also conventional and color-enabled digital camera 20 connected to the computer R captures the original V lying on the supporting plate 12 and produces a high-resolution digital color image of the whole or at least the relevant region of the original. For opaque originals, the illumination arrangement 22 provides for the illumination of the original during the scanning by the digital camera. In the case of transparent originals, the illumination arrangement found in the base is used.

Figure 2:
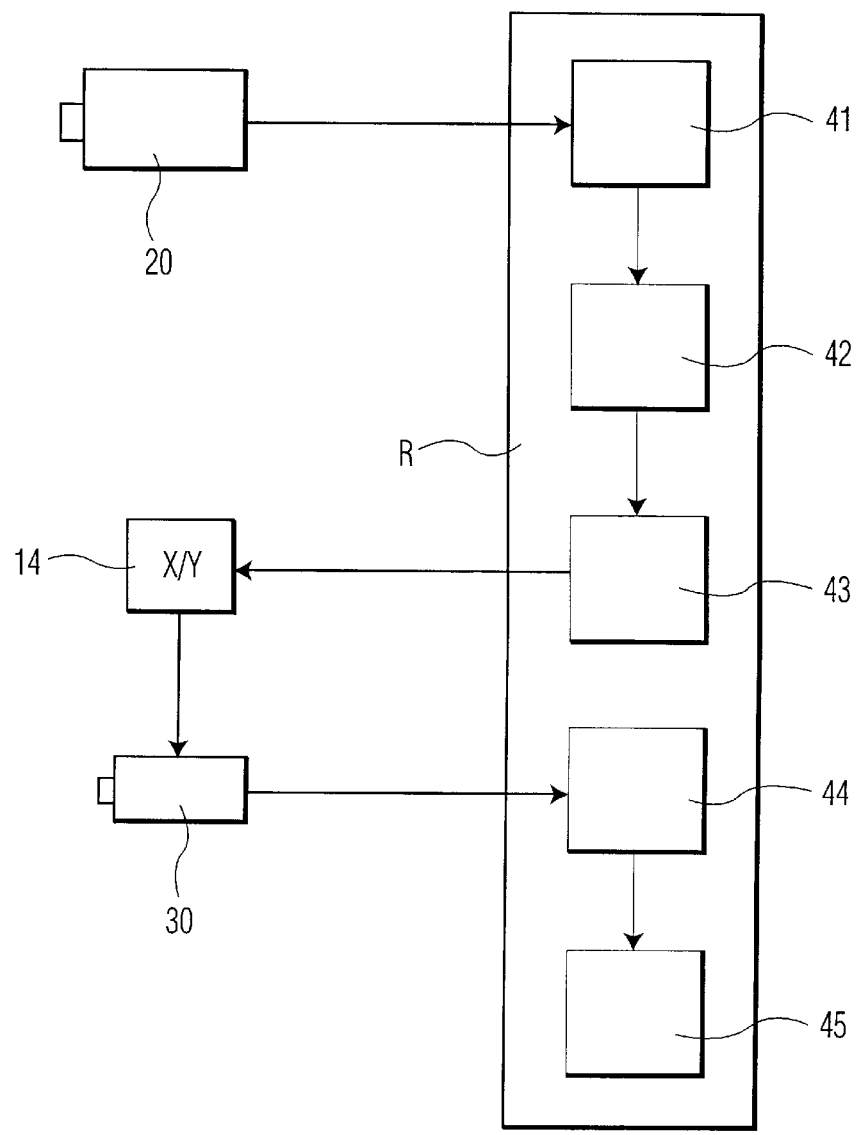
FIG. 2 is a schematic illustration of the process in accordance with the invention.

The cooperation of the individual components of the measuring apparatus as well as the basic principle of the measuring process in accordance with the invention are schematically illustrated in FIG. 2.

Initially, the original V is photoelectrically scanned pixel by pixel under the control of the computer R and by way of the digital camera 20, and a digital color representation 41 of the original V is produced from the scanning data obtained and stored in the computer R. The bridge 13 and the spectral measuring head 30 are thereby in an at rest position when they are located outside the capturing region of the digital camera. The totality of all measuring positions 43 at which the original is to be colorimetrically measured by way of the spectral measuring head 30 is then determined by the computer R from this color representation 41 according to generally known image processing methods and by way of a suitable analysis software 42 using previously stored reference data from originals. This is described in more detail further below. On the basis of the measuring positions 43 obtained in this manner, the computer R then controls in a generally known manner the drive structures overall referred to by 14 for the displacement of the bridge 13 and the spectral measuring head 30 and thereby successively moves the spectral measuring head 30 to all measuring positions. A measurement is initiated at each measuring position. The spectral measurement data obtained thereby and referred to in their entirety by 44 are read into the computer R and stored therein for further processing by a suitable processing program 45, for example, one for the generation of apparatus profiles.

The described procedures apply principally in the same manner for the measurement of opaque as well as transparent originals, the principle difference being essentially only the manner of illumination of the original respectively during the image generating scanning with the digital camera and the spectral measurement with the spectral measuring head.

In the context of this invention, the term high-resolution means that the size of the scanning points of the image generating unit, in this embodiment the digital camera 20, is significantly smaller, especially by a factor of more than 10 smaller, than the measurement aperture of the color measuring head 30.

Figure 3:
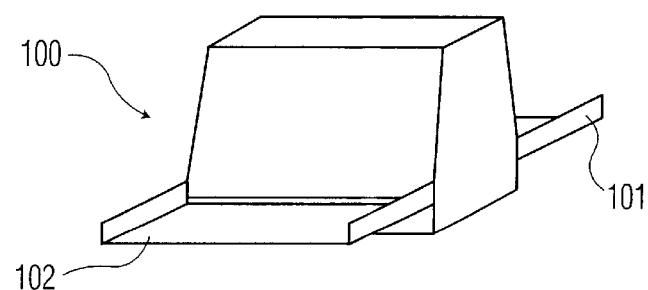
FIG. 3 is an overall isometric view of a second embodiment of the measuring apparatus in accordance with the invention.
Figure 4:
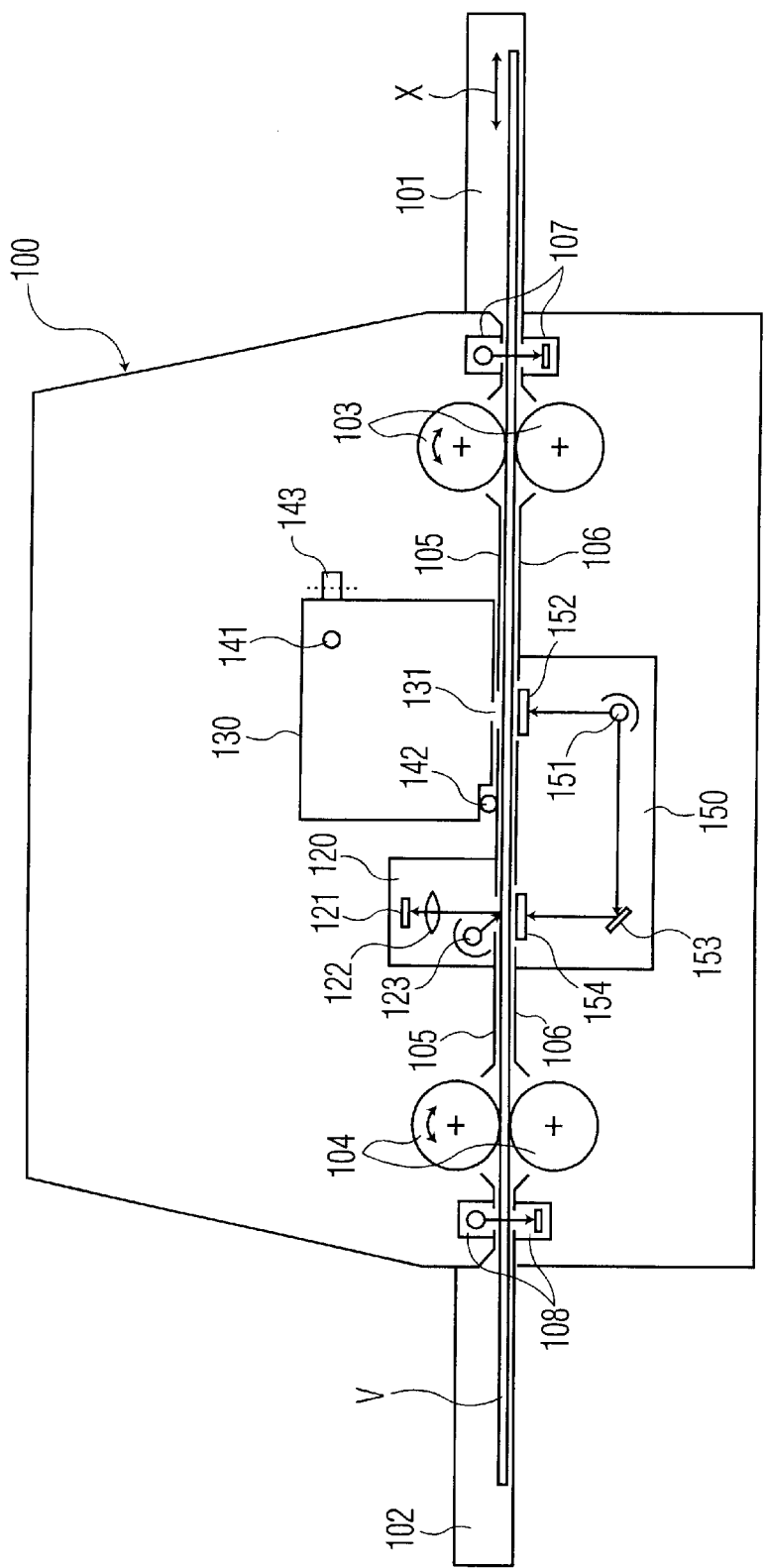
FIG. 4 is a schematic longitudinal section through the measuring apparatus shown in FIG. 3.
Figure 5:
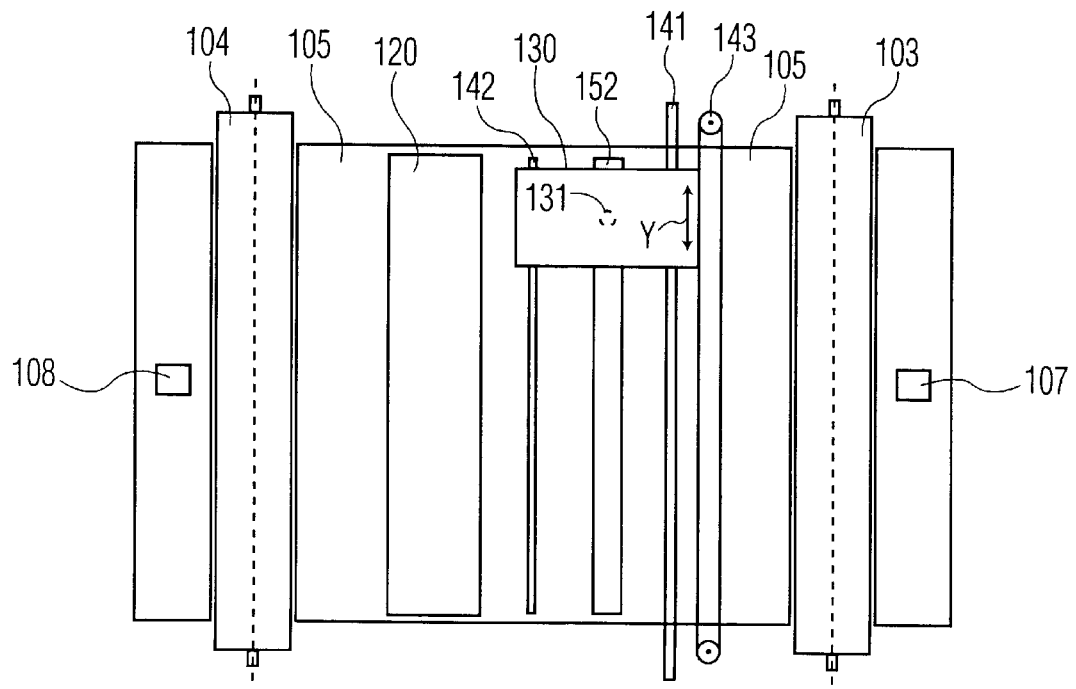
FIG. 5 is a top plan view of the measuring apparatus shown in FIG. 3 with the device cover removed.
Figure 6:
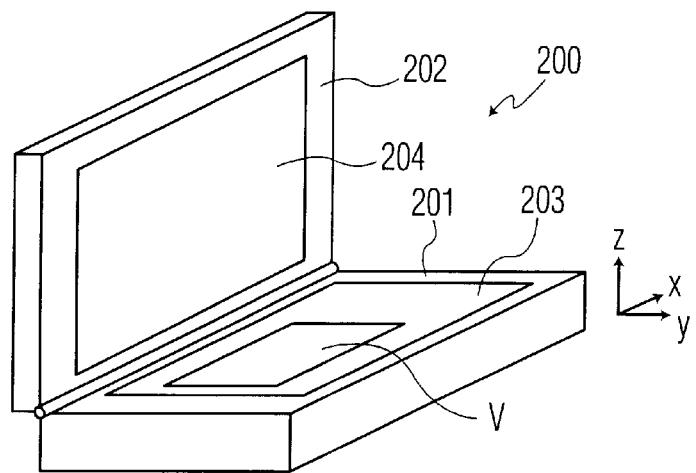
FIG. 6 is an overall isometric view of a third embodiment of the measuring apparatus in accordance with the invention.

An embodiment of the measuring apparatus in accordance with the invention and according to the principle of an autofeed scanner is schematically illustrated in FIGS. 3–5. The measurement illustrated includes a housing 100 and an input tray 101 and an output tray 102 at two opposing sides thereof, which are positioned essentially in the same plane. An original transport mechanism is found inside the housing 100 which includes two motor driven roller pairs 103 and 104, guides 105 and 106 and two light barriers 107 and 108. The transport mechanism for the original is controlled by a here not illustrated conventional internal control in combination with an external computer and allows the transport of an original V inserted into the input tray 101 in direction of the arrow X along an essentially planar path defined by the guides 105 and 106 through the housing and into the output tray 102, and reverse.

The housing 100 further includes a color-enabled image producing unit or photoelectric scanning device in the form a linear scanning array (line camera) 120 which is in the movement path of the original V and stationary and which extends over the whole width of the original V (transverse to the direction of advancement X), so that the whole width can be captured. The image producing unit or line camera 120 can be constructed, for example, in a generally known manner as a color-enabled CIS (Contact Image Sensor). It typically includes an optoelectric line sensor 121, an optical imaging unit 122 and an illumination 123 for the top illumination measurement of opaque originals. The image producing unit 120 scans the original pixel by pixel transverse to the direction of transport X of the latter (in direction of the arrow Y, FIG. 5) whereby the second scanning dimension is captured by the advancement of the original. The image producing unit is connected with the internal control and the external computer, in a manner generally known and the computer reads in the scanning signal produced and produces therefrom and stores a digital color representation of the original.

The measuring apparatus so far essentially corresponds to a conventional color-enabled autofeed scanner for opaque originals so that the person skilled in the art does not require any further explanation in relation thereto.

According to a further important aspect of the invention, a principally known color or spectral measuring head 130 is provided in the housing apart from the image producing unit 120 which head is reciprocatable by a displacement unit transverse to the transport direction X of the original V in direction of the arrow Y (FIG. 5) and over the whole width of the original. The conventionally constructed displacement unit consists of a guide axle 141, a support 142 and a motor driven drive belt 143 (FIG. 5) and is controlled by the external computer in a manner also generally known. The displacement unit allows adjustment of the position of the color or spectral measuring head 130 transverse to and over the whole width of the original.

The color or spectral measuring head 30 can be provided with all technologies generally used in colorimetrics. It typically consists of an illumination unit which is preferably constructed as a 45° ring illumination and a pickup channel which feeds the light to be measured at 0° to a module which carries out this spectral selection. The wavelength selection is preferably carried out with a diode row spectrometer or with a set of interference filters. A further wavelength selection method is based on the use of LEDs with different wavelengths as illumination and a spectral broadband photoelectric receiver. Such a spectrometer is described, for example, in U.S. Pat. No. 6,043,893, the disclosure of which is hereby incorporated by reference in its entirety.

By transverse adjustment of the color measuring head 130 in the Y direction by way of the displacement unit and by longitudinal movement of the original in the X direction by way of the original transport mechanism, the color measuring head 130 can be positioned at any desired measuring position of the original V and the original can be colorimetrically (or spectrally) measured at those measuring positions by way of the measuring head. The control of the positioning of the color measuring head 130 is again achieved as in the first embodiment, by the computer on the basis of the measuring positions derived from the digital color representation of the original.

In order to be also able to measure transparent originals, an additional illumination arrangement 150 is provided below the measuring aperture 131 of the color measuring head 130. This arrangement includes a light source 151 which extends transverse to the original (for example a fluorescent tube or a linear arrangement of light emitting diodes) and a diffuser 152 which extends along the movement path of the color measuring head 130 directly opposite the measuring aperture thereof. The illumination arrangement 150 can at the same time also be a transmission illumination for the image producing unit or line camera 120 and for that purpose includes deflection optics 153 and a further diffuser 154 which extends below and along the image producing unit. Of course, separate transmission illuminations can also be provided for the color measuring head 130 and the image producing unit 120, for example for space reasons.

FIGS. 6–9 schematically illustrate an embodiment of the measuring device in accordance with the invention constructed according to the principle of a flatbed scanner. It consists on the one hand of a superstructure as is conventional in flatbed scanners and on the other hand of a color measuring head which is moveable over the whole area of the original. The difference to an autofeed scanner essentially only consists in that the original is stationary and the linear scanning array is moveably arranged relative to the original.

The superstructure 200 consists of a base 201 and a flip-up cover 202 with a white insert 204 which serves as background for remission measurements. The base 201 includes a housing, which at the top is closed by a glass plate 203 on which the original V to be measured is positioned. Under the glass plate (FIG. 7) is positioned an image producing unit in the form of a linear scanning array (line camera) 220 which is preferably constructed as a CIS (Contact Image Sensor) and itself consists of an optoelectric line sensor 221, an optical imaging unit 222 and an illumination unit 223 for the top illumination measurement of opaque originals. The line sensor extends in Y direction and is positioned so that it can capture the whole width of the original.

Figure 8:
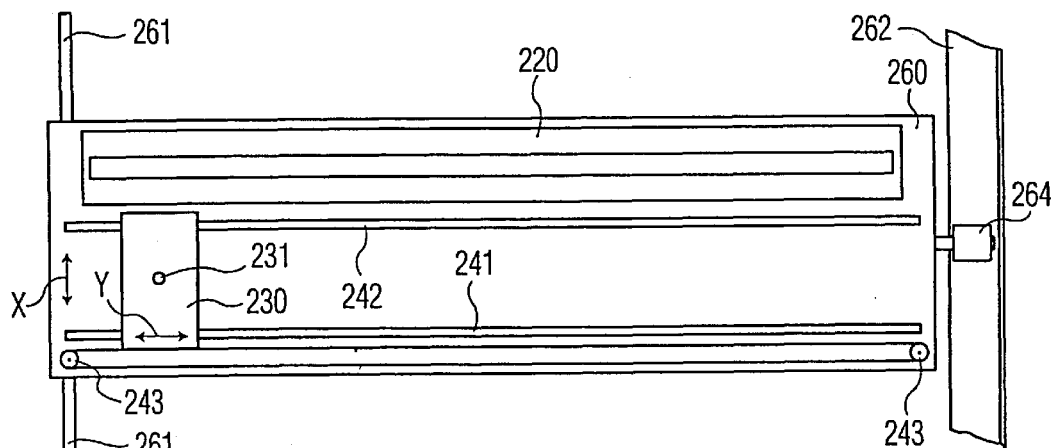
FIG. 8 is a schematic top plan view rotated by 900 according to the line VIII-VIII in FIG. 7.

In addition to the scanning line 220, a spectrally operating color measuring head 230 with a measuring aperture 231 is moveably positioned on a displacement unit parallel to the scanning line 220, ie. moveable in direction of the arrow Y. The displacement unit is essentially of conventional construction and includes a guide axle 241, a support 242 and a motor driven drive belt 243 (FIG. 8). The displacement unit allows the adjustment of the color or spectral measuring heads 230 transverse to and over the whole width of the original.

Figure 7:
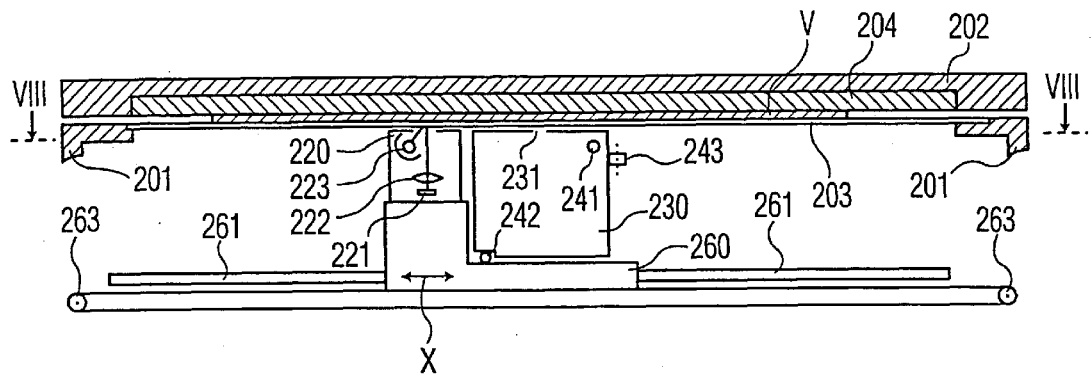
FIG. 7 is a schematic longitudinal section through the measuring apparatus shown in FIG. 6 with the cover closed.

The image producing unit or scanning line 220 and the color measuring head 230 are themselves mounted on a second displacement unit, which consists of a sled 260, a guide axle 261, a support 262 (FIG. 7), a roller 264 (FIG. 8) and a motor driven drive belt 263 (FIG. 7).

This second displacement unit allows the displacement of the scanning line 220 together with the color measuring head 230 in direction of the arrow X so that they can scan the whole original V.

The displacement units, the scanning line and the color measuring head are controlled in a manner generally known in the art as in the preceding embodiments by a not illustrated conventional internal control in combination with an external computer.

Figure 9:
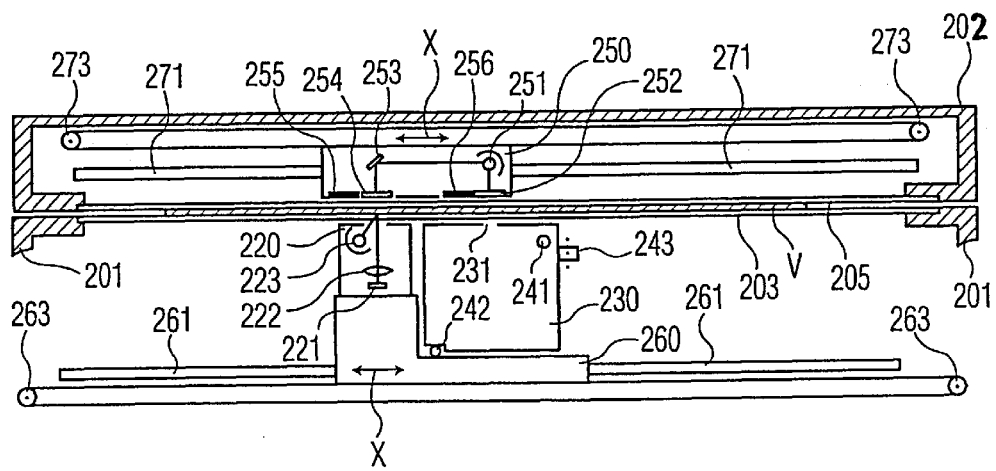
FIG. 9 is a schematic longitudinal section through a variant of the measuring apparatus shown in FIG. 6 with the cover closed.

In order to also carry out measurements on transparent originals, the embodiment of the measuring apparatus in accordance with the invention sketched in FIG. 9 is provided with an additional illumination arrangement 250, in the cover 202 of the superstructure which perfectly serves at the same time the scanning line 220 and the color measuring head 230, analog to the embodiment of the FIGS. 3–5. Furthermore, a transparent plate 205 is provided in place of the white insert 204. The illumination arrangement 250 includes a light source 251 extending transverse to the original (for example a fluorescent tube), a diffuser 252, redirecting optics 253 and a further diffuser 254 as well as black backgrounds 255 and 256. The illumination arrangement 250 is positioned on a further displacement unit which is essentially of the same construction as that for the joint displacement of scanning line 220 and color measuring head 230 in X direction and consists of a guide axle 271 and a motor driven drive belt 273. The additional illumination arrangement 250 is moved during the scanning or colorimetric measurement parallel and synchronously to the scanning line 220 or to the color measuring head 230 in direction of the arrow X. Depending on the relative position of the additional illumination unit 250, remission measurements can be carried out with white or black background.

With the exception of the presence of the color measuring head 230, the measuring apparatus essentially corresponds in construction and function to a conventional color-enabled flatbed scanner for opaque or transparent originals so that the person skilled in the art does not require any further explanation in relation thereto. The control of the individual components of this embodiment is carried out analog to the autofeed scanner embodiment by the conventional internal control in combination with an external computer and, thus, does also not need any special discussion.

The measuring process in accordance with the invention will be described in the following by way of the example of the measuring of an opaque color test chart (test chart) in more detail (remission measurement).

The test chart to be measured is positioned on the measuring apparatus in accordance with the invention according to one of the described embodiments. Using the digital camera 20 or the scanning line 120 or 220, a color image of the test chart is recorded generally in a conventional manner and stored in the computer. With the computer, this color image is analyzed using image processing methods, whereby the type of the test chart as well as the exact location of the individual color fields (measuring positions) are determined. Algorithms which can carry out this task are sufficiently known today and described in the pertinent literature.

A possible approach for the analysis of the test chart is as follows:

A first approximation of the coordinates of the color fields is first calculated by segmentation of fields of the same color as well as the determination of their main focus. For the segmentation of the fields, one can use the fact that the color fields of a test chart are normally of the same size. The information so obtained on the structure of the color test chart (location and color of the color fields) is then compared with reference data of color test charts (stored in the computer) and the type of the color test chart is determined. Since the nominal location of the color fields is now known from the structure of the reference chart, the previously calculated location of each individual color field can be tested and noticeable artifacts in the image created by segmentation errors, and therefore positioning errors, can be eliminated.

Subsequently, the colorimetric data and possibly the spectrum at the measuring positions are determined with the color measuring head 30 or 130 or 230 and preferably stored in the computer in a text file of defined format. For example, an ICC profile can be calculated from these colorimetric data of the original with a generally known software.

The procedure for the measuring of a transmission test chart is analog to the above described remission measurement. In addition, the inhomogeneity of the transmission illumination is measured with the scanner or the digital camera and the spectral measurement data detected by the color measuring head are compensated therewith. Prior to the insertion of the transmission test chart (slide, film, foil, . . . ) into the scanner according to FIGS. 3–9 or on the measurement table according to FIG. 1, the light distribution of the transmission illumination is measured with the image producing unit and stored. Thereafter the test chart is positioned into the scanner or onto the measurement table and an image thereof is recorded. This image is analyzed with the computer using image processing methods, whereby the type of the test chart as well as the exact location of the individual color fields is determined (see above). Subsequently, the colorimetric values and/or the spectrum of the color fields are determined at the identified locations with the color measuring head. Artifacts in the spectral measurement data, which can be caused by the locally not-constant (inhomogeneous) transmission illumination, can be subsequently compensated by way of the previously recorded data of the image of the light distribution of the transmission illumination. An ICC profile of a foil printer can then be calculated, for example, from the colorimetric data so obtained.

A further important aspect of the invention is the possibility of measurement within the image for the calculation of control references for the control of output apparatus, for example printing machines. For the control of printing machines by way of "measurement within the image", as described in, for example, EP-A 0 914 945, the disclosure of which is hereby incorporated by reference in its entirety, spectral scanners are used today, which detect the complete spectrum of each pixel. Although this is a very elegant method, it is very cost intensive because of the complex hardware of a spectral scanner. A spectral scanner of the company Heidelberger Druckmaschinen suitable for this purpose is described, for example, in EP-A 0 847 187.

The combination in accordance with the invention of a digital camera or a scanner with a color or spectral measuring head moveable in X and Y direction can deliver comparable results at noticeably lower technical cost than is required for a complete spectral scanner and with only slightly increased required time.

A typical sequence of the control of an output apparatus by spectral measurement in the image is described in the following.

The prepress data of the original to be printed are taken over in digital form (for example in PDF or CIP3 format). By way of suitable algorithms, those pixels within the image which are best suited for the control because of their color composition (layer structure) and homogeneity of the image region are automatically determined in a generally known manner. The user can be given the possibility of modifying these pixels (adding, erasing, or moving pixels). A first printed sheet is then output and placed on the measuring apparatus in accordance with the invention. Depending on the embodiment, an image of the printed sheet is recorded with a scanner or a digital camera. This image is correlated with the prepress data whereby the positions of the pixels to be spectrally measured on the original can be very exactly determined without interaction with the user. At the so found measuring positions, the colorimetric information is now determined with the spectral measuring head and the control references for the output apparatus are determined therefrom with suitable algorithms in a known manner. A new sheet is output with the new adjustments of the output apparatus according to these control references and measured as described above and the control parameters adjusted, if required, until the required quality is achieved. Thereafter, sheets are measured only at predetermined intervals and the control parameters are adjusted, if required, in order to guarantee a consistent quality of the output.

The positioning of a color measuring head or spectral measuring head in an essentially conventional transmission scanner according to the embodiment of the FIGS. 6–9 results in a very cost efficient construction of a spectral XY-transmission scanner, since the same illumination and the same X-displacement mechanism can be used for the scanning line of the scanner and the spectral measuring head.

The combination in accordance with the invention of an image producing apparatus (scanner or digital camera) with a color measuring head for the colorimetric measurement of test charts has a series of advantages over the apparatus previously used for this purpose and described above:

The user does not need to provide data on the position of the color fields (measurement positions) and the type of test chart, since this information is determined from the image data of the original by way of image processing methods. This approach increases user friendliness and eliminates a potential source of errors.

The location of the color fields can be very exactly determined by the local resolution of the scanner or the digital camera which is higher than that achievable with a scanning color measuring head. The smallest colorimetrically measurable color field size can thereby be selected to be only insignificantly larger than the measurement aperture of the color measuring head without creating false measurements by incorrect positioning and, thus, coevaluation of the light from adjacent fields. Small fields enable a larger number of color fields for a given original size, which is advantageous for the quality of the ICC profile.

Since the location of the color fields need not be detected by multiple measurements with the color measuring head as is the case in scanning handheld measuring apparatus or strip measuring apparatus, the time required for the capturing of the colorimetric values is significantly reduced.

No requirements exist for a special positioning of the color fields such as for example a minimal delta E between two fields which is a prerequisite for the use of scanning measuring apparatus. Since the test chart after the measurement is not only colorimetrically but also digitally available as a high resolution image, artifacts created by dirt or scratches can be detected in the colorimetric measurement data and ignored, corrected or measured again.

With test charts having inhomogeneous color fields (large colorimetric variations within the individual measurement fields) the accuracy of the colorimetric values can be significantly increased with the color measuring head by multiple measurement at different locations in the field and subsequent averaging. The homogeneity of the individual color fields can be determined by analysis of the image data of the original. If it is low, the quality can be maintained within an acceptable range by automatic multiple measurement.

By capturing the inhomogeneity of the illumination with the image producing unit (scanning line or digital camera) instead of (as in the prior art) with a spectral measuring head, the measurement time can be significantly shortened.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. Process for the colorimetric measurement of a two dimensional original at predetermined measuring positions, comprising the steps of:
   photoelectrically scanning the original pixel by pixel by way of a color-enabled photoelectric scanning device to produce a digital color representation of the original;
   determining at least one measuring position from the digital color representation;
   moving a color measuring head being movable under computer control relative to the original two-dimensionally to the at least one measuring position; and
   colorimetrically measuring the original at the measuring position.

2. Process according to claim 1, wherein a scanning resolution of a scanning arrangement used for the scanning is selected such that scanning points are smaller than a measurement aperture of the color measuring head.

3. Process according to claim 1, wherein the scanning device is a digital camera.

4. Process according to claim 1, wherein the scanning device is one of a line-by-line operating autofeed scanner and a flatbed scanner.

5. Process according to claim 1, wherein the color measuring head is a spectral measuring head.

6. Process according to claim 1, wherein digital image processing methods are used for determining the measuring position from the digital color representation of the original.

7. Process according to claim 1, wherein the original is an opaque or transparent color measuring chart.

8. Process according to claim 1, comprising the further steps of illuminating the original with a transmission light illumination, measuring light distribution of the transmission light illumination with the scanning device, and correcting the spectral measurement data determined by the color measuring head by way of the measured light distribution for compensating an inhomogeneity of the light distribution of the transmitted light illumination.

9. Process according to claim 1, including the further step of recognizing artifacts created by dirt or scratches in the digital color representation and correcting colorimetric measurement data to remove the artifacts.

10. Apparatus for the colorimetric measurement of a two-dimensional original, comprising:

a color-enabled photoelectric scanning device for pixel by pixel photoelectric scanning of a whole original;

a computer for producing a digital color representation from scanning data produced by the scanning device and for determining measuring positions from the digital color representation;

a color measuring head for colorimetric measurement of the original at the measuring positions;

means for moving the original and the color measuring head two-dimensionally relative to one another; and a computer for controlling the means for moving, for initiating a measurement and reading in measurement data produced by the color measuring head, and for storing the measurement data.

11. Apparatus according to claim 10, wherein the scanning device has a resolution such that scanning points are smaller than a measuring aperture of the color measuring head.

12. Apparatus according to claim 10, wherein the scanning device is a digital camera.

13. Apparatus according to claim 10, wherein the scanning device is one of a line-by-line operating autofeed scanner and a flatbed scanner.

14. Apparatus according to claim 10, wherein the color measuring head is a spectral measuring head.

15. Apparatus according to claim 10, wherein the computer determining the measuring positions from the digital color representation of the original by using digital image processing methods.

* * * * *